United States Patent [19]

Ichinose et al.

[11] Patent Number: 5,258,404
[45] Date of Patent: Nov. 2, 1993

[54] 3-(UNSUBSTITUTED OR SUBSTITUTED BENZYL)-1-ALKYL-2-OXOCYCLOPENTANE CARBOXYLIC ACID ALKYL ESTER DERIVATIVES, METHOD FOR PREPARATION FUNGICIDES, AND USE THEREOF AS INTERMEDIATE COMPOUNDS

[75] Inventors: Isao Ichinose, Fukushima; Masanori Minoguchi, Tokyo; Satoru Kumazawa; Eyji Yoshida, both of Fukushima, all of Japan

[73] Assignee: Kureha Chemical Industry Co., Ltd., Tokyo, Japan

[21] Appl. No.: 945,718

[22] Filed: Sep. 16, 1992

[30] Foreign Application Priority Data

Sep. 18, 1991 [JP] Japan .................. 3-267073

[51] Int. Cl.$^5$ .................. A01N 37/34; C07C 255/00; C07C 205/00
[52] U.S. Cl. .................... 514/522; 514/530; 514/535; 514/545; 558/414; 560/21; 560/51
[58] Field of Search .................. 560/51, 21; 558/414; 514/522, 530, 535, 545

[56] References Cited

U.S. PATENT DOCUMENTS 4,938,792 7/1990 Kumazawa et al. .............. 71/76

FOREIGN PATENT DOCUMENTS 026778 5/1988 European Pat. Off. .
0413448 2/1991 European Pat. Off. .

OTHER PUBLICATIONS

Chemical Abstracts, vol. 113, No. 9, (1990) Abstract No. 78396.

Primary Examiner—José G. Dees
Assistant Examiner—Dwayne C. Jones
Attorney, Agent, or Firm—Burgess Ryan & Wayne

[57] ABSTRACT

Disclosed is a 3-(unsubstituted or substituted benzyl)-1-alkyl-2-oxocyclopentane carboxylic acid alkyl ester derivative as represented by the general formula (I):

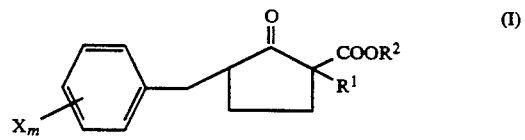

where
$R^1$ and $R^2$ are each a lower alkyl group;
X is a halogen atom, a cyano group, an alkyl group, a haloalkyl group, a phenyl group or a nitro group; and
m is 0 or an integer from 1 to 5 and when m is greater than 1 each X can be the same or different.

Further, disclosed is a method for the preparation of the compound (I) by carrying out the benzylation, rearrangement, and alkylation from the 2-oxocyclopentane carboxylic acid alkyl ester derivative without isolation of any intermediate compound. In addition, a fungicide is provided in which the 3-(unsubstituted or substituted benzyl)-1-alkyl-2-oxocyclopentane carboxylic acid alkyl ester derivatives (I) is contained as an active ingredient.

Furthermore, it can provide 2-(unsubstituted or substituted benzyl)-5-alkylcyclopentanone derivatives from the 3-(unsubstituted or substituted benzyl)-1-alkyl-2-oxocyclopentane carboxylic acid alkyl ester derivatives (I).

13 Claims, No Drawings

3-(UNSUBSTITUTED OR SUBSTITUTED BENZYL)-1-ALKYL-2-OXOCYCLOPENTANE CARBOXYLIC ACID ALKYL ESTER DERIVATIVES, METHOD FOR PREPARATION FUNGICIDES, AND USE THEREOF AS INTERMEDIATE COMPOUNDS

BACKGROUND OF THE INVENTION

1. Field of the Invention

The present invention relates to 3-(unsubstituted or substituted benzyl)-1-alkyl-2-oxocyclopentane carboxylic acid alkyl ester derivatives, a method for the preparation of the same, a fungicide containing the same, and a use thereof as intermediate compounds.

2. Description of the Related Art

EP-A-294,222 (the Japanese counterpart being Japanese Patent Laid-open Publication (kokai) No. 79,117/1989), U.S. Pat. No. 4,938,792 (the Japanese counterpart being Japanese Patent Laid-open Publication (kokai) No. 93,574/1989 and the European counterpart being EP-A-267,778), and EP-A-341,954 (the Japanese counterpart being Japanese Patent Laid-open Publication (kokai) No. 42,003/1990) disclose a 2-(unsubstituted or substituted benzyl)-5-alkylcyclopentanone derivative as represented by the general formula (VII):

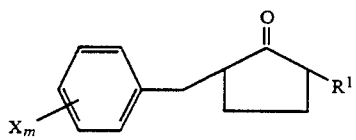
(VII)

where $R^1$ is a lower alkyl group;
X is a halogen atom, a cyano group, an alkyl group, a haloalkyl group or a nitro group; and
m is 0 or an integer of 1 to 5 and when m is greater than 1 each X can be the same or different,
which can be employed as intermediate compounds for pesticides, medicine, and the like.

U.S. Pat. No. 4,938,792 (Japanese Patent Laid-open Publication (kokai) No. 93,574/1989 and the European counterpart being EP-A-267,778) contains a detailed description of reaction schemes (i) and (ii), as will be described hereinafter, for the preparation of a 2-(unsubstituted or substituted benzyl)-5-alkylcyclopentanone derivative as represented by the general formula (VII'):

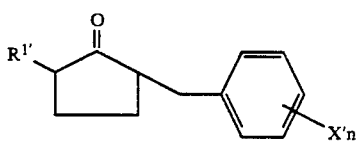
(VII')

where
$R^{1'}$ is a $C_1$–$C_5$ alkyl group;
$X'$ is a halogen atom, a $C_1$–$C_5$ alkyl group or a phenyl group; and n is 0, 1 or 2.

The reaction scheme (i) for the preparation of the 2-(unsubstituted or substituted benzyl)-5-alkylcyclopentanone derivative as represented by the general formula (VII') involves benzylating a 2-oxocyclopentane carboxylic acid alkyl ester derivative as will be represented by the general formula (II') with an unsubstituted or substituted benzyl halide as will be represented by the general formula (III'); alkylating the resulting 1-(unsubstituted or substituted benzyl)-2-oxocyclopentane carboxylic acid alkyl ester derivative as will be represented by the general formula (IV') with an alkyl halide; hydrolyzing the ester group of the resulting 3-alkyl-1-(unsubstituted or substituted benzyl)-2-oxocyclopentane carboxylic acid alkyl ester derivative as will be represented by the general formula (VIII); and decarboxylating the resulting compound, thereby giving the 2-(unsubstituted or substituted benzyl)-5-alkylcyclopentanone derivative as represented by the general formula (VII').

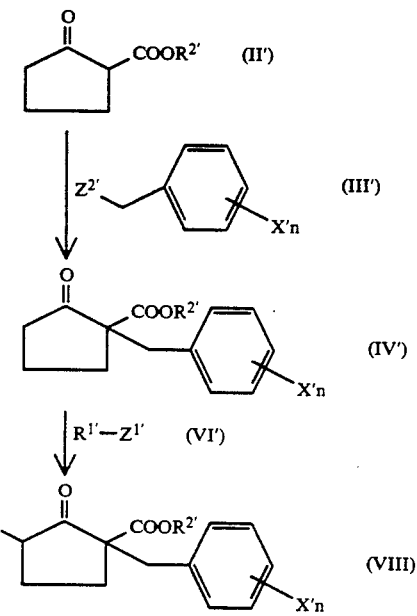

where
$R^{2'}$ is a $C_1$–$C_3$ alkyl group;
$Z^{1'}$ and $Z^{2'}$ are each a halogen atom; and
$R^{1'}$, $X'$ and n have the same meaning as above.

The reaction scheme (ii) for the preparation of the 2-(unsubstituted or substituted benzyl)-5-alkylcyclopentanone derivative as represented by the general formula (VII') involves benzylating a 3-alkyl-2-oxocyclopentane carboxylic acid alkyl ester derivative as will be represented by the general formula (IX) with the unsubstituted or substituted benzyl halide as represented by the general formula (III'); hydrolyzing the ester group of the resulting 3-alkyl-1-(unsubstituted or substituted benzyl)-2-oxocyclopentane carboxylic acid alkyl ester derivative as will be represented by the general formula (VIII); and decarboxylating the resulting compound, thereby giving the compound as represented by the general formula (VII').

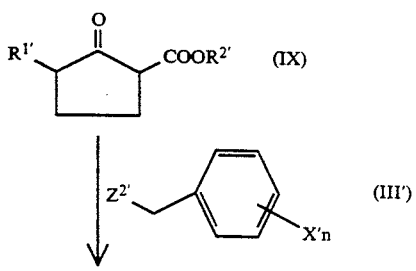

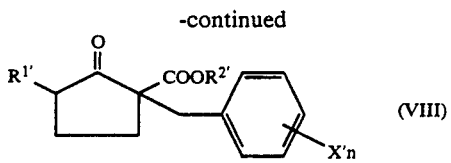

where

R[1'], R[2'], X', Z[2'] and n have the same meaning as above.

In order to provide good yield in the method as indicated in the reaction schemes as have been described hereinabove, the alkylation in the reaction scheme (i) should be carried out by using a strong base such as sodium hydride or the like in an aprotic solvent; and the reaction in the reaction scheme (ii) should be carried out in a reaction scheme, as will be described hereinafter, by alkylating a 2-oxocyclopentane carboxylic acid alkyl ester derivative as will be represented by the general formula (II') with the alkyl halide as represented by the general formula (VI') in the presence of a base; subjecting the resulting 1-alkyl-2-oxocyclopentane carboxylic acid alkyl ester derivative as will be represented by the general formula (X) to rearrangement in a lower alcohol in the presence of an alkali metal lower alkoxide; and isolating the resulting 3-alkyl-2-oxocyclopentane carboxylic acid alkyl ester derivative as represented by the general formula (IX):

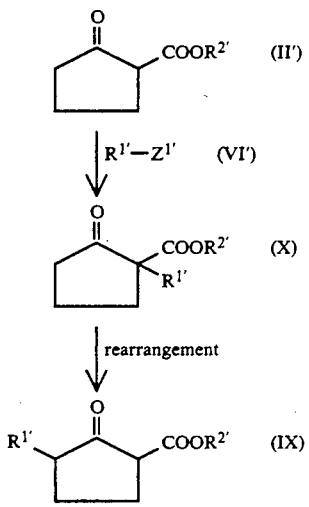

where

R[1'], R[2'], and Z[1'] have the same meaning as above.

In order to provide precursors of the 2-(unsubstituted or substituted benzyl)-5-alkylcyclopentanone derivatives as represented by the general formula (VII') and the 3-alkyl-1-(unsubstituted or substituted benzyl)-2-oxocyclopentane carboxylic acid alkyl ester derivatives as represented by the general formula (VIII) with high yield, a strong base such as sodium hydride and the like should be employed or the intermediate compounds should be isolated and purified from the reaction scheme.

Particular care should be required, however, in using sodium hydride in a large quantity because hydrogen is caused to occur during the reaction of the sodium hydride. Further, the isolation and the purification of the intermediate compounds require a post-treatment step in the reaction so that it suffers from the disadvantage in terms of preparation because the reaction step is increased.

Hence, strong demands have been made to provide a method in which the yield of the product is not reduced, a which is easily and readily handled can be employed, and the isolation and purification of the intermediate compound are not required to thereby reduce the reaction steps.

SUMMARY OF THE INVENTION

The present invention has been accomplished to meet the demands as have been described hereinabove. Therefore, the first object of the present invention is to provide a precursor of a 2-(unsubstituted or substituted benzyl)-5-alkylcyclopentanone derivative as represented by the general formula (VII), which can be prepared through a method in which a base that can be handled with ease is employed, any intermediate compound need not be isolated and purified, and the number of reaction steps is small.

The second object of the present invention is to provide a method for the preparation of the precursor from the 1-(unsubstituted or substitued benzyl)-2-oxocyclopentane carboxylic acid alkyl ester derivative as represented by the general formula (IV).

Further, the third object of the present invention is to provide a method for the preparation of the precursor from the 2-oxocyclopentane carboxylic acid alkyl ester derivative as represented by the general formula (II).

In addition, the fourth object of the present invention is to provide a method capable of easily producing the 2-(unsubstituted or substituted benzyl)-5-alkylcyclopentanone derivative as represented by the general formula (VII) from the precursor.

The fifth object of the present invention is to provide a novel use of the precursor as a fungicide, particularly an agricultural and horticultural fungicide, in addition to a use as an intermediate compound for pesticides, medicine and the like.

Extensive research and review have been made with the attempt to find a base which is more easily handled than sodium hydride and to reduce the reaction steps without necessitating the isolation and purification of any intermediate compound in preparing the precursor of the 2-(unsubstituted or substituted benzyl)-5-alkylcyclopentanone derivative as represented by the general formula (VII).

As a result, it has been found that a 3-(unsubstituted or substituted benzyl)-1-alkyl-2-oxocyclopentane carboxylic acid alkyl ester derivative as will be represented by the general formula (I) can be utilized as a precursor for the compound as represented by the general formula (VII) in the reaction scheme as will be indicated as follows:

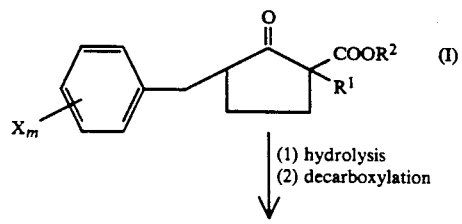

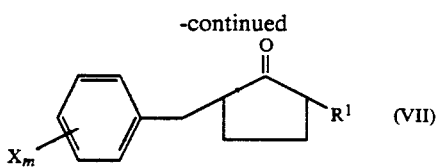

where
R¹, R², X and m have the same meaning as above.

Further, it is found that the compound (I) can be prepared with high yield by subjecting the 2-oxocyclopentane carboxylic acid alkyl ester derivative as represented by the general formula (II) to benzylation with an alkali metal lower alkoxide as represented by the general formula (III), rearrangement, and alkylation, without the isolation and purification of any intermediate compound in each of the reaction steps, in a reaction scheme as will be described hereinafter.

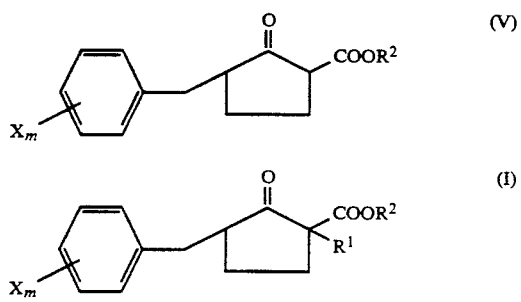

where
Z¹ and Z² are each a halogen atom; and
R¹, R², X and m have the same meaning as above.

The first object of the present invention is achieved by providing a novel 3-(unsubstituted or substituted benzyl)-1-alkyl-2-oxocyclopentane carboxylic acid alkyl ester derivative as represented by the general formula (I) as follows:

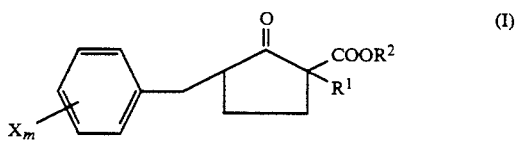

where
R¹ and R² are each a lower alkyl group;
X is a halogen atom, a cyano group, an alkyl group, a haloalkyl group, a phenyl group or a nitro group; and
m is 0 or an integer from 1 to 5 and when m is greater than 1 each X can be the same or different.

The second object of the present invention can be achieved by providing a method for continuously carrying out rearrangement and alkylation in the reaction scheme as indicated hereinabove, wherein the rearrangement is carried out to convert the 1-(unsubstituted or substituted benzyl)-2-oxocyclopentane carboxylic acid alkyl ester derivative as represented by the general formula (IV) into the 3-(unsubstituted or substituted benzyl)-2-oxocyclopentane carboxylic acid alkyl ester derivative as represented by the general formula (V) in the presence of the alkali metal lower alkoxide in the lower alcohol; and wherein the alkylation is carried out to alkylate the resulting compound (V) with the alkyl halide as represented by the general formula (VI), after distillation of the lower alcohol, to give the 3-(unsubstituted or substituted benzyl)-1-alkyl-2-oxocyclopentane carboxylic acid alkyl ester derivative as represented by the general formula (I).

Further, the third object of the present invention can be achieved by providing a method for continuously carrying out benzylation, rearrangement and alkylation in the reaction scheme as indicated hereinabove, wherein the benzylation being carried out to benzylate the 2-oxocyclopentane carboxylic acid alkyl ester derivative as represented by the general formula (II) with the unsubstituted or substituted benzyl halide as represented by the general formula (III) in the presence of the alkali metal base; wherein the rearrangement is carried out in the lower alcohol in the presence of the alkali metal lower alkoxide to convert the 1-(unsubstituted or substituted benzyl)-2-oxocyclopentane carboxylic acid alkyl ester derivative as represented by the general formula (IV) into the 3-(unsubstituted or substituted benzyl)-2-oxocyclopentane carboxylic acid alkyl ester derivative as represented by the general formula (V); and wherein the alkylation is carried out to alkylate the resulting compound (V) with the alkyl halide as represented by the general formula (VI), after distillation of the lower alcohol, to give the 3-(unsubstituted or substituted benzyl)-1-alkyl-2-oxocyclopentane carboxylic acid alkyl ester derivative as represented by the general formula (I).

In addition, the fourth object of the present invention can be achieved by providing a method for the preparation of the 2-(unsubstituted or substituted benzyl)-5-alkylcyclopentanone derivative as represented by the general formula (VII) by hydrolyzing the 3-(unsubstituted or substituted benzyl)-1-alkyl-2-oxocyclopentane carboxylic acid alkyl ester derivative as represented by the general formula (I) and then decarboxylating the compound (I) to give the compound (VII).

Furthermore, the fifth object of the present invention can be achieved by providing a fungicide containing the 3-(unsubstituted or substituted benzyl)-1-alkyl-2-oxocyclopentane carboxylic acid alkyl ester derivative as represented by the general formula (I) as an active ingredient.

Other objects, features and advantages of the present invention will become apparent in the course of the description of the preferred embodiments, which follows.

DESCRIPTION OF THE PREFERRED EMBODIMENTS

The 3-(unsubstituted or substituted benzyl)-1-alkyl-2-oxocyclopentane carboxylic acid alkyl ester derivative according to the present invention may be represented by the general formula (I):

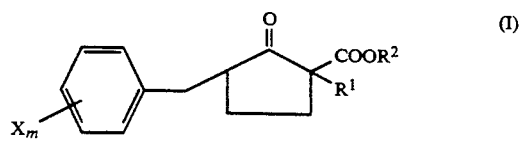

where
R¹ and R² are each a lower alkyl group;
X is a halogen atom, a cyano group, an alkyl group, a haloalkyl group, a phenyl group or a nitro group; and m is 0 or an integer from 1 to 5 and when m is greater than 1 each X can be the same or different.

The substituents $R^1$ and $R^2$ may be identical to or different from each other and each may be a saturated or unsaturated lower alkyl group, which is intended to mean a monovalent, straight-chained or branched, saturated or unsaturated hydrocarbon residue; it may preferably include a $C_1$-$C_4$ alkyl group and it may more preferably include methyl, ethyl, propyl, and isopropyl. The term "halogen atom" referred to in this specification is intended to mean, for example, chlorine atom, bromine atom, fluorine atom, and the like. Preferred is chlorine atom, and more preferred is chlorine atom joined in the 4-position of the benzene ring. The term "alkyl group" referred to hereinabove is intended to mean the lower alkyl group as have been described hereinabove. The term "haloalkyl group" referred to hereinabove is intended to mean the lower alkyl group referred to hereinabove, in which one hydrogen atom or more is or are substituted with the halogen atom referred to hereinabove, preferably with fluorine atom. The reference symbol "m" may be 0 or an integer from 1 to 5, preferably 0 or 1.

The 3-(unsubstituted or substituted benzyl)-1-alkyl-2-oxocyclopentane carboxylic acid alkyl ester derivatives as represented by the general formula (I) include the following specific compounds as will be described in Table 1 below:

TABLE 1

| Compound Nos. | Substituents of General Formula (I) | | |
|---|---|---|---|
| | $R^1$ | $R^2$ | Xm |
| I-1 | $CH_3$ | $CH_3$ | 4-Cl |
| I-2 | $(CH_3)_2CH$ | $CH_3$ | 4-Cl |

Note: The term "4-Cl" means a substitution of chlorine in the 4-position of the phenyl group.

The 3-(unsubstituted or substituted benzyl)-1-alkyl-2-oxocyclopentane carboxylic acid alkyl ester derivatives as represented by the general formula (I) may be prepared from the 2-oxocyclopentane carboxylic acid alkyl ester derivatives as represented by the general formula (II) in the reaction scheme as will be shown hereinafter.

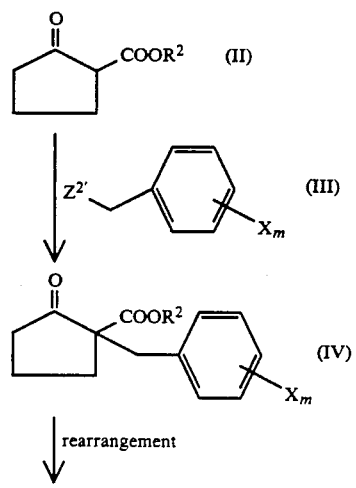

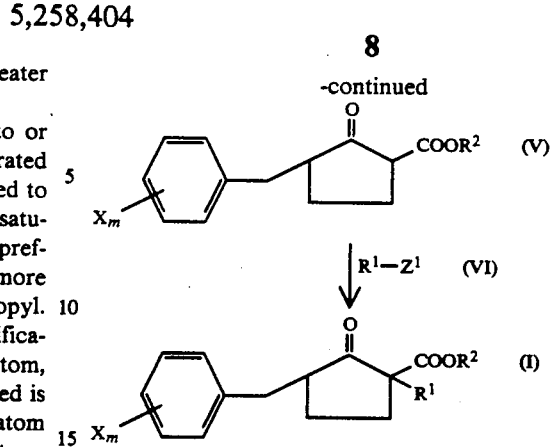

where
$Z^1$ and $Z^2$ are each a halogen atom; and
$R^1$, $R^2$, X, and m have the same meaning as above.

In the reaction scheme as indicated hereinabove, an alkyl metal base is added preferably at the rate of 1.0 to 1.2 moles equivalent to the 2-oxocyclopentane carboxylic acid alkyl ester derivative (II). When the alkali metal lower alkoxide is employed, the lower alcohol is azeotropically distilled off with an appropriate solvent such as toluene and the compound (II) is then benzylated with the unsubstituted or substituted benzyl halide (III). If the halide is not an iodide, it is preferred to use an alkali metal iodide in a catalytic amount. The alkali metal alkoxide may include, for example, sodium methoxide, potassium methoxide, sodium ethoxide, sodium isopropoxide, potassium t-butoxide, and the like.

The solvent to be employed in this reaction may include, for example, an aromatic hydrocarbon such as toluene, xylene, etc., a nitrile such as acetonitrile, etc., an amide such as dimethylformamide, dimethyl acetamide, N-methylpyrrolidone, etc., and the like. The solvents may be employed singly or in combination of two or more.

The reaction may be carried out at temperatures in the range of from approximately 50° C. to 100° C., preferably from approximately 70° C. to 90° C.

To the reaction mixture containing the 1-(unsubstituted or substituted benzyl)-2-oxocyclopentane carboxylic acid alkyl ester derivative (IV) obtained by the benzylation are added the lower alcohol and the alkali metal lower alkoxide at the rate of 1.0 to 1.2 moles equivalent, and the mixture was heated under reflux to carry out the rearrangement into the 3-(unsubstituted or substituted benzyl)-2-oxocyclopentane carboxylic acid alkyl ester derivative (V). After the lower alcohol has been distilled off, the 3-(unsubstituted or substituted benzyl)-2-oxocyclopentane carboxylic acid alkyl ester derivative (V) is then alkylated with the alkyl halide (VI) to give the 3-(unsubstituted or substituted benzyl)-1-alkyl-2-oxocyclopentane carboxylic acid alkyl ester derivative (I). As the alkyl halide (VI), there may be mentioned, for example, methyl bromide, methyl iodide, ethyl iodide, propyl bromide, isopropyl iodide, n-butyl chloride, isobutyl bromide and the like.

If the halide employed in this alkylation is not an iodide, it is preferred to use a catalytic amount of an alkali metal iodide. As the solvent to be employed for the rearrangement, the lower alcohol may be employed singly or in combination with other organic solvent as have been described hereinabove, such as an aromatic hydrocarbon or the like.

After the completion of the rearrangement, an aromatic hydrocarbon such as toluene is added, and the lower alcohol is distilled off. It can be noted herein that, even if the aromatic hydrocarbon would be left in the reaction mixture, it does not adversely affect the alkylation which follows.

The alkylation may be carried out in the solvent, and the solvent to be employed therefor may include, for example, a nitrile solvent such as acetonitrile, etc., an amide solvent such as methylformamide, dimethylformamide, dimethyl acetamide, N-methylpyrrolidone, etc., a sulfur-containing compound such as dimethylsulfoxide, sulfolane etc., an alcohol such as t-butyl alcohol, and the like. These solvents may be employed singly or in combination of two or more.

The reaction may be carried out at temperatures in the range of from approximately 50° C. to 100° C., preferably from approximately 60° C. to 90° C.

The resulting 3-(unsubstituted or substituted benzyl)-1-alkyl-2-oxocyclopentane carboxylic acid alkyl ester derivative as represented by the general formula (I) may be isolated from the resulting reaction mixture by usual procedures for the isolation of a compound, such as column chromatography, recrystallization, and the like. These procedures may be employed solely or in combination with the other procedures.

The resulting 3-(unsubstituted or substituted benzyl)-1-alkyl-2-oxocyclopentane carboxylic acid alkyl ester derivatives as represented by the general formula (I) can be hydrolyzed and then decarboxylated to give the 2-(unsubstituted or substituted benzyl)-5-alkylcyclopentanones derivatives as represented by the general formula (VII) with ease and high yield in the reaction scheme as will be indicated hereinafter, which are useful as intermediate compounds for pesticides, medicine and the like.

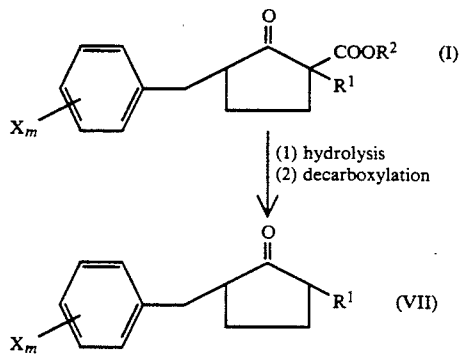

where
$R^1$, $R^2$, X, and m have the same meaning as above).

The hydrolysis and the decarboxylation can be carried out in either acidic or basic conditions.

When the reaction is to be carried out in acidic conditions, it is desired to use acetic acid as a solvent, in addition to water. A catalyst may be employed, and the catalyst may include, for example, an inorganic acid such as hydrochloric acid, hydrobromic acid and the like. The reaction may be carried out at temperatures ranging from approximately 50° C. to its reflux point, preferably from approximately 80° C. to its reflux point.

The 3-(unsubstituted or substituted benzyl)-1-alkyl-2-oxocyclopentane carboxylic acid alkyl ester derivatives as represented by the general formula (I) are used as a fungicidal composition, and are generally used in the form of dust, wettable powder, granules, emulsion and the like with carriers or other adjuvants. In such a case, the preparations are prepared so as to contain one or more of the compound (I) of the present invention in an amount of 0.1% to 95% by weight, preferably, 0.5% to 90% by weight, and more preferably 2% to 70% by weight.

The auxiliary agent to be employed for the preparation may include, for example, a carrier, a diluent, a surfactant and the like, which have conventionally been employed as auxiliary agents for the preparation of fungicides. The carrier in a solid form may include, for example, talc, kaolin, bentonite, diatomaceous earth, white carbon, clay, and the like; the diluent in a liquid form may include, for example, water, xylene, toluene, chlorobenzene, cyclohexane, cyclohexanone, dimethylsulfoxide, dimethylformamide, an alcohol, and the like.

The surfactant may preferably be chosen depending upon the forms of the preparations and their effects; an emulsifiable agent may include, for example, polyoxyethylene alkyl aryl ether, polyoxyethylene sorbitan monolaurate, and the like; a dispersing agent may include, for example, a lignin sulfonate, dibutylnaphthalene sulfonate, and the like; and a wetting agent may include, for example, an alkyl sulfonate, an alkylbenzene sulfonate, and the like.

The above preparations are classified into those which can be used directly, and those which are used after diluting so as to have a suitable concentration with a diluent such as water, etc. The concentration of the present compounds in case of using after diluting is preferred to be in a range of 0.001%–1.0%.

Further, the application dosage of the compound of this invention is in a range of 20 g–5,000 g and preferably 50 g–1,000 g per 1 ha of agricultural and horticultural land such as farm, paddy field, fruit garden, hothouse, etc.

It is of course possible to increase and decrease the concentration and the application dosage beyond the above-mentioned ranges, because they depend upon the form of preparations, method of application, place to be used, target crops, etc.

It is further to be noted that the compounds (I) according to the present invention may be employed in combination with other active compounds, such as fungicides, bactericides, insecticides, miticides, herbicides, and the like.

A specific description will now be made of examples of the preparation of the 3-(unsubstituted or substituted benzyl)-1-alkyl-2-oxocyclopentane carboxylic acid alkyl ester derivatives (I) according to the present invention, examples of uses as intermediate compounds, examples of preparations and examples of tests.

The present invention is not limited to the following examples.

The present invention will first be described by way of examples of the preparation of the specific compounds.

PREPARATION EXAMPLE 1

Preparation of Methyl 3-(4-chlorobenzyl)-1-methyl-2-oxocyclopentane Carboxylate (I-1)

To a solution of 2.6671 grams (0.01 mole) of methyl 1-(4-chlorobenzyl)-2-oxocyclopentane carboxylate in 8 ml of anhydrous methanol was added 2.1 ml of sodium methoxide (a 28% (by weight) methanol solution), and the mixture was heated with reflux for 30 minutes.

To the resulting reaction mixture was added 20 ml of toluene, and methanol was azeotropically distilled off under reduced pressure from the reaction mixture. Thereafter, 4 ml of anhydrous dimethylformamide (DMF) and 1.5642 grams (0.011 mole) of methyl iodide were added to the resulting mixture.

After the temperature was elevated to 60° C. and the mixture was stirred for 1 hour, the reaction mixture was poured into water with ice cubes and then extracted with ethyl acetate. The resulting organic layer was then washed with 1N-hydrochloric acid and a saturated sodium hydrogen carbonate aqueous solution.

After drying over anhydrous sodium sulfate, the solvent was distilled off under reduced pressure, leaving a yellow oily material in the amount of 2.9826 grams.

The oily material was then purified with silica gel column chromatography, thereby yielding methyl 3-(4-chlorobenzyl)-1-methyl-2-oxocyclopentane carboxylate (I-1) in the amount of 2.2616 grams (0.0081 mole).

The percentage yield and the physical properties of the compound (I-1) are as follows:

Yield: 81%

Colorless, transparent oily substance

IR (firm, $\nu_{max}$): 2956, 2880, 1756, 1732, 1496, 1452, 1274, 1160, 1094, 1016, 848, 804 cm$^{-1}$ $^1$H-NMR (CDCl$_3$): δ 1.17, 1.35 (s,3H), 1.56-1.85 (m, 2H), 1.90-2.12 (m, 1H), 2.28-2.71 (m, 3H), 3.06-3.15 (m, 1H), 7.08, 7.10 (d, 2H, J=8.30 Hz), 7.25 (d, 2H, J=8.30 Hz)

PREPARATION EXAMPLE 2

Preparation of Methyl 3-(4-chlorobenzyl)-1-isopropyl-2-oxocyclopentane carboxylate (I-2)

To a solution of 2.6671 grams (0.01 mole) of methyl 1-(4-chlorobenzyl)-2-oxocyclopentane carboxylate in 8 ml of anhydrous methanol was added 2.1 ml of sodium methoxide (a 28% (by weight) methanol solution), and the mixture was heated with reflux for 30 minutes.

To the resulting reaction mixture was added 20 ml of toluene, and methanol was azeotropically distilled off under reduced pressure from the reaction mixture. Thereafter, 2 ml of anhydrous dimethylformamide (DMF), 0.5 ml of t-butanol, and 2 ml (0.02 mole) of isopropyl iodide were added to the resulting mixture.

After the temperature was elevated to 60° C. and the mixture was stirred for 5 hours, the reaction mixture was poured into ice water and then extracted with ethyl acetate. The resulting organic layer was then washed with 1N-hydrochloric acid and a saturated sodium hydrogen carbonate aqueous solution.

After drying over anhydrous sodium sulfate, the solvent was distilled off under reduced pressure, leaving a yellow oily material in the amount of 2.7762 grams.

The oily material was then purified with silica gel column chromatography, thereby yielding methyl 3-(4-chlorobenzyl)-1-isopropyl-2-oxocyclopentane carboxylate (I-2) in the amount of 2.4058 grams (0.0078 mole).

The percentage yield and the physical properties of the compound (I-2) are as follows:

Yield: 78%

Colorless, transparent oily substance IR (firm, $\nu_{max}$): 2960, 2870, 1745, 1720, 1490, 1460, 1250, 1225, 1160, 1095, 1016, 845, 804, 790, 760 cm$^{-1}$ $^1$H-NMR (CDCl$_3$): δ 0.78, 0.81 (d, 3H, J=7.32 Hz), 0.84, 0.87 (d, 3H, J=7.32 Hz), 1.5-1.8 (m, 2H), 2.01 (m, 1H), 2.2-2.4 (m, 2H), 2.5-2.7 (m, 2H), 3.08 (dd, 1H, J=13.67, 3.91 Hz), 3.62, 3.70 (s, 3H), 7.06, 7.10 (d, 2H, J=8.30 Hz), 7.23, 7.26 (d, 2H, J=8.30 Hz)

PREPARATION EXAMPLE 3

Preparation of Methyl 3-(4-chlorobenzyl)-1-isopropyl-2-oxocyclopentane carboxylate (I-2)

To a solution of 3.41 grams (0.024 mole) of methyl 2-oxocyclopentane carboxylate in 20 ml of anhydrous methanol was added 5.3 ml of sodium methoxide (a 28% (by weight) methanol solution), and the mixture was heated with reflux for 30 minutes.

To the resulting reaction mixture was added 68 ml of toluene, and methanol was azeotropically distilled off under reduced pressure from the reaction mixture. Thereafter, 10 ml of toluene, 2 ml of anhydrous dimethylformamide (DMF), 3.9495 grams (0.025 mole) of p-chlorobenzyl chloride, and 0.3965 mg of potassium iodide were added to the resulting mixture.

After the solvent was distilled off, 10 ml of anhydrous methanol and 5.3 ml of sodium methoxide (a 28% (by weight) methanol solution) were added, followed by heating the resulting mixture under reflux for 30 minutes.

To the resulting reaction mixture was added 70 ml of toluene, and thereafter methanol was azeotropically distilled off, followed by the addition of 17.5 ml of anhydrous dimethylformamide (DMF), 2 ml of t-butanol and 4.8 ml (0.048 mole) of isopropyl iodide.

After the temperature was elevated to 60° C. and the resulting mixture was stirred for 5 hours, the reaction mixture was poured into water with ice cubes and extracted with ethyl acetate. The resulting organic layer was then washed with 1N-hydrochloric acid and a saturated sodium hydrogen carbonate aqueous solution.

After drying over anhydrous sodium sulfate, the solvent was distilled off, leaving a crude product in the amount of 7.2389 grams.

As a result of gas chromatography by the internal standard method, this crude product was found to contain methyl 3-(4-chlorobenzyl)-1-isopropyl-2-oxocyclopentane carboxylate (I-2) in the yield of 65%.

REFERENCE PREPARATION EXAMPLE

Preparation of 2-(4-chlorobenzyl)-5-isopropylcyclopentanone (VII-1)

To a solution of 1.4026 grams (4.27 mmole) of methyl 3-(4-chlorobenzyl)-1-isopropyl-2-oxocyclopentane carboxylate in 1.8 ml of isopropyl alcohol and 0.84 ml of toluene was added 2.36 ml of a 5N sodium hydroxide solution, and the mixture was heated at 80° C. for 5 hours.

After cooling, the resulting reaction mixture was admixed with 30 ml of water and then extracted twice with 30 ml of ethyl acetate. The resulting organic layer was washed with water and sodium chloride.

After the organic layer was dried over anhydrous sodium sulfate, the solvent was distilled off under reduced pressure, leaving a yellow oily material in the amount of 0.8711 grams.

As a result of gas chromatography by the internal standard method, this crude product was found to be as pure as 96.34% by weight and to contain 3-(4-chlorobenzyl)-5-isopropylcyclopentanone (VII-1) in the yield of 78.4%.

The following examples are directed to the formulations or preparations containing the 3-(unsubstituted or substituted benzyl)-1-alkyl-2-oxocyclopentane carboxylic acid alkyl ester derivative as represented by the general formula (I) as an active ingredient.

FORMULATION EXAMPLE 1

Dust

| Compound No. I-1 | 3 parts by weight |
|---|---|
| Clay | 40 parts by weight |
| Talc | 57 parts by weight |

The above-mentioned ingredients were mixed to prepare a dust.

FORMULATION EXAMPLE 2

Wettable Powder

| Compound No. I-2 | 50 parts by weight |
|---|---|
| Lignin sulfonate | 5 parts by weight |
| Alkyl sulfonate | 3 parts by weight |
| Diatomaceous earth | 42 parts by weight |

The above-mentioned ingredients were mixed to prepare a wettable powder. This preparation was used in situ by diluting it with water.

FORMULATION EXAMPLE 3

Granules

| Compound I-1 | 5 parts by weight |
|---|---|
| Bentonite | 43 parts by weight |
| Clay | 45 parts by weight |
| Lignin sulfonate | 7 parts by weight |

The above-mentioned ingredients were mixed and kneaded with adding water thereto. The mixture was granulated by means of an extrusion granulating machine, followed by drying to obtain granules.

FORMULATION EXAMPLE 4

Emulsion

| Compound I-2 | 20 parts by weight |
|---|---|
| Polyoxyethylene alkyl aryl ether | 10 parts by weight |
| Polyoxyethylene sorbitan monolaurate | 3 parts by weight |
| Xylene | 67 parts by weight |

The above-mentioned ingredients were mixed and dissolved to obtain an emulsion.

Antifungal Tests:

The compounds as represented by the general formulas (I-1) and (I-2) were tested for anti-fungal activities against various plant pathogens.

Test Procedures:

Each of the compounds as represented by the general formulas (I-1) and (I-2) was dissolved in dimethylsulfoxide in a suitable concentration, 0.6 ml of the solution was well mixed with 60 ml of a PAS culture medium at about 60° C. in a 100 ml conical flask, and the resultant mixture was poured into petri dishes and was caused to coagulate, by which plate culture media containing the compound of this invention were obtained.

On the other hand, plate culture media on which test fungi were previously cultured were punched by a cork borer so as to have a diameter of 4 mm, followed by inoculating on the above-mentioned plate culture medium. After inoculation was carried out, they were incubated for 1-3 days at a preferable temperature for each fungus and growth of fungi was observed by measuring the diameter of the colony. Hyphae elongation inhibitory rates were determined respectively in accordance with the below described equation:

$$R = 100(dc - dt)/dc$$

where
- R = Hyphae elongation inhibitory rate (%)
- dc = Diameter of colony on the non-treated plate culture medium
- dt = Diameter of colony on the plate culture medium containing the tested compound Test results were ranked in three stages by the following ranking system.
- 0: R is lower than 40%;
- 1: R is between 40% and 80%; and
- 2: R is higher than 80%.

The results against the test fungi will be shown in Table 2 below.

TABLE 2

| Compound Nos. | Concentration (μg/ml) | Test Fungi | | |
|---|---|---|---|---|
| | | H.s. | R.s. | S.c. |
| I-1 | 100 | 1 | 1 | 1 |
| I-2 | 100 | 1 | 1 | 1 |

The abbreviations for the test fungi in Table 2 above are as follows:
- H.s.: *Helminthosporium sigmoideum*
- R.s.: *Rhizoctonia solani*
- S.c.: *Sclerotinia sclerotirum*

What is claimed is:

1. A 3-(unsubstituted or substituted benzyl)-1-alkyl-2-oxocyclopentane carboxylic acid alkyl ester derivative as represented by the general formula (I):

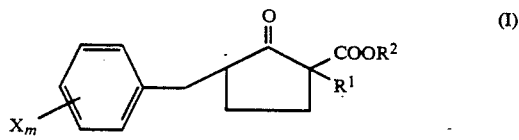

where
- $R^1$ and $R^2$ are each a lower alkyl group;
- X is a halogen atom, a cyano group, an alkyl group, a haloalkyl group, a phenyl group or a nitro group; and
- m is 0 or an integer from 1 to 5 and when m is greater than 1 each X can be the same or different.

2. A 3-(unsubstituted or substituted benzyl)-1-alkyl-2-oxocyclopentane carboxylic acid alkyl ester derivative as claimed in claim 1, wherein $R^1$ is methyl or isopropyl, $R^2$ is methyl, X is chlorine atom, and m is 1.

3. A 3-(unsubstituted or substituted benzyl)-1-alkyl-2-oxocyclopentane carboxylic acid alkyl ester derivative as claimed in claim 1, wherein the substituent X is located in the 4-position of the phenyl group.

4. The carboxylic acid alkyl ester derivative of claim 1 which is methyl 3-(4-chlorobenzyl)-1-methyl-2-oxocyclopentane carboxylate.

5. The carboxylic acid alkyl ester derivative of claim 1 which is methyl 3-(4-chlorobenzyl)-1-isopropyl-2-oxocyclopentane carboxylate.

6. A fungicidal composition comprising a fungicidally effective amount of a 3-(unsubstituted or substituted benzyl)-1-alkyl-2-oxocyclopentane carboxylic alkyl ester of the formula:

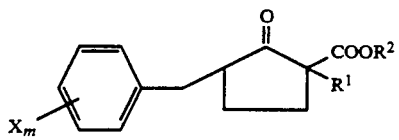

where $R^1$ and $R^2$ are independently each a lower alkyl group;

x is independently selected from the group consisting of halo, cyano, alkyl, haloalkyl, phenyl, and nitro; m is 0 or an integer from 1 to 5; and a fungicidally acceptable adjuvant.

7. The fungicidal composition of claim 6, wherein $R^1$ is methyl or isopropyl, $R^2$ is methyl, x is chloro and m is 1.

8. The fungicide as claimed in claim 6 wherein the X substituent is located in the 4-position of the phenyl group.

9. The fungicide as claimed in claim 6 wherein the carboxylic acid alkyl ester derivative is methyl 3-(4-chlorobenzyl)-1-methyl-2-oxocyclopentane carboxylate.

10. The fungicide as claimed in claim 6 wherein the carboxylic acid alkyl ester derivative is methyl 3-(4-chlorobenzyl)-1-isopropyl-2-oxocyclopentane carboxylate.

11. A method for inhibiting the growth of fungi which comprises contacting said fungi with a fungi-inhibiting-effective amount of the fungicide of claim 6.

12. The method of claim 11 wherein the carboxylic acid alkyl ester derivative is methyl 3-(4-chlorobenzyl)-1-methyl-2-oxocyclopentane carboxylate.

13. The method of claim 11 wherein the carboxylic acid alkyl ester derivative is methyl 3-(4-chlorobenzyl)-1-isopropyl-2-oxocyclopentane carboxylate.

* * * * *